(12) United States Patent
Siracusa

(10) Patent No.: US 7,476,262 B2
(45) Date of Patent: Jan. 13, 2009

(54) OLEIC ACID FREE HAIR DYE

(76) Inventor: Jack Siracusa, 67 Trade Zone Dr., Ronkonkoma, NY (US) 11779

( * ) Notice: Subject to any disclaimer, the term of this patent is extended or adjusted under 35 U.S.C. 154(b) by 0 days.

(21) Appl. No.: 12/075,567

(22) Filed: Mar. 12, 2008

(65) Prior Publication Data

US 2008/0222820 A1    Sep. 18, 2008

Related U.S. Application Data

(60) Provisional application No. 60/906,299, filed on Mar. 12, 2007.

(51) Int. Cl.
*A61Q 5/10* (2006.01)

(52) U.S. Cl. ........................ 8/405; 8/406; 8/435; 8/551; 8/558; 8/587

(58) Field of Classification Search ............... 8/405, 8/406, 435, 551, 558, 587
See application file for complete search history.

(56) References Cited

FOREIGN PATENT DOCUMENTS

FR          2867974  A1  *  9/2005

\* cited by examiner

*Primary Examiner*—Eisa B Elhilo
(74) *Attorney, Agent, or Firm*—Grimes & Battersby, LLP; James F. McLaughlin

(57) ABSTRACT

A new and improved hair dye formula which is completely oleic acid free and has a high percentage water base including sodium lauryl sulfate, sodium lauryl sulfoacetate and disodium laureth sulfosuccinate along with a low percentage peroxide content for protecting consumers during the hair dye process.

1 Claim, No Drawings

OLEIC ACID FREE HAIR DYE

CROSS REFERENCES TO RELATED APPLICATIONS

This application claims priority benefit of a U.S. Provisional Application, Ser. No. 60/906,299, filed in the United States Patent and Trademark Office on Mar. 12, 2007, and entitled "Oleic-free coloring additive and improved dying function thereof."

STATEMENT REGARDING FEDERALLY SPONSORED RESEARCH

Not Applicable

REFERENCE TO APPENDIX

Not Applicable

BACKGROUND OF THE INVENTION

1. Field of the Invention

The present invention relates to a hair care product for coloring hair in a new and unique way, and more particularly to a hair dye product which is very different from the prior art in that it is completely oleic acid free.

Personal appearance may well be one of the most important and definitive statements an individual can showcase to the world. It is the first thing that others sense about another person; and it is often used to make a variety of assumptions about that person, whether those assumptions are correct or not. Needless to say, a great number of people are concerned with how they appear to others. In this vein, people alternatively attempt to conform their looks to some standard, or attempt to differentiate their appearance away from what is considered the norm.

One of the ways individuals may enhance or alter their appearance is through the style and color of their hair. Many individuals, both male and female, style their hair with shapes and color to achieve a desired look. Not surprisingly, the quantity of hair styling products, salons and hair styling professionals is great.

Market Research

The overall U.S. hair care market is projected to be worth nearly $7.5 billion at retail in 2005. That record sum will result from steady growth of roughly 3% or 4% during each year of the period 2000 through 2005. The compound annual growth rate (CAGR) for the time frame will be 3.7%."

With the above statistics in mind, the hair care coloring segment was one of the most dynamic product categories in 2001 "as baby boomers, gen X, gen Y women, as well as more men than ever before, are more frequently experimenting with hair color.

Coloring has generated some $1.4 billion worth of business through food, drug and mass, according to IRI.

Industry estimates placed U.S. salon hair coloring revenues at $10 billion out of a total of $46 billion in 1999. Read "New fashion of salon has Subway as mode." Palm Beach Post. Com (Jun. 6, 2003)

The incidence of hair color has been rising and is now at 50 percent, said Liz Read, senior director of hair color marketing at Clairol. Of those who color, 36 percent color their hair at home.

C&EN reports that with these improvements, hair dyeing has become one of the fastest growing segments of the personal care market. U.S. retail sales of home dyeing kits grew at double-digit rates in the 1990s and hit $1.6 billion in 2001, estimates industry consultant Kline & Co. The global hair dye market is now at some $7.2 billion, according to market research firm Euro monitor.

L'Oreal has about half of the U.S. hair dye market and the Clairol unit of Procter & Gamble controls 40 percent, says Meyer R. Rosen, president of Interaction Consulting. Dye suppliers say interest in hair dyeing is growing so fast that they expect other consumer products companies to enter the market.

Kline Project Manager Carrie Bonner says that a recent study of consumer buying habits showed that 37 percent of those surveyed had used hair dyes in the previous year and that 42 percent of American women and 25 percent of American men use dyes. Hair dyes are most popular among people aged 16-20 (48 percent), with the next largest group of users in the 40-49 range (45 percent). Only 24 percent of those over 60 use hair dyes.

2. Prior Art

The following symptoms and problems are well known in the prior art:

Brittle Hair: Detergent type base which removes the oils and de-fats the hair and scalp creating dry brittle hair and scalp condition, which may flake giving the appearance of dandruff.

Drying: The incorporation of alcohol, as example, isopropanol or ethanol, additionally tends to dry the hair and scalp, as does the soap base.

Damage: The use of ammonia causes the hair to swell allowing the dyes to enter the hair shaft but also damaging the hair. Many individuals experience sever tingling, itching, or burning of the scalp during the process and at times along period after. The 6% peroxide level needed to open the hair shaft for the dyes to enter causes undue damage to the hair in addition to the itching and burning of the scalp.

Allergic reactions: A heavy concentration of the oxidation hair dyes, Up to 8-10% to make up for the loss of dyes reacting in the base itself rather than within the hair shaft. The possibility of eczema or contact dermatitis showing up on the face and around the hair line, face swelling up and painful bruising that often requires hospital treatments.

Staining: Due to the high concentration of dye needed to overcome the reaction and loss of dye in the base rather than within the hair shaft, staining of the forehead and area around the face require extreme protection. Removing of the stain requires a great deal of effort and at times severe abrasion of the affected area.

Required Dye Time: Present products require the mixture to remain on the hair a minimum of 30 minutes for total penetration.

Warm wearing: All hair dyes continue to oxidation process weeks later and the dyes tend toward the red. In time the limited amount of dye within the hair shaft is overwhelmed.

Conditioning; due to a combination of all the reasons listed a conditioning is required to bring the hair back to a healthy looking state.

It is an object of the within inventive hair dye to overcome the foregoing and other shortcomings of the prior art hair dyes.

To this end the formula of the within inventive hair dye contains the following ingredients.

New Formulation:
Dye shares same as prior art but lower concentration about 1-3 maximum.
Activator: Standard 3% peroxide rather than prior art of 6%.
Of particular note, the within inventive hair dye has a base formula with a water content of no less than 90% as compared to prior art brands of 30%.

Demonstrated benefits of the new formula:
1. Empirical evidence and laboratory testing show that a system containing large amounts of water greatly reduces or entirely eliminates the possibility of brittle hair, drying and staining.
2. Damage to the hair is greatly reduced due to the elimination of ammonia with monoethanolamine.
3. Allergic reaction or contact dermatitis is virtually eliminated since the concentration of dyes has been reduced from 10% to 3%, in addition the majority of the reaction takes place away from the scalp in the hair shaft. Having the base almost color less as compared to competitive brands.
4. The required dye times has been reduced to 10 to 15 minutes as compared to 30 minutes require by prior art. This greatly reduced the possibility of an allergic reaction, staining, and damage. Any staining encounter is easily removed with a damp soapy cloth.
5. Conditioning agents are virtually eliminated, as the difficulties inherent in the present brands are no longer present. The dyed hair has a more natural look and feel.
6. Since this is a water base formula the frequently encountered unpleasant odor, burning, and itching are replaced with a cool non-irritating feeling during the dyeing process.
7. The problem of warm wearing is virtually eliminated since the concentration of dye within the hair shaft is so great any shift toward the red is overwhelmed by the unaffected color.

Further Benefits of the Oleic Acid Free Hair Dye Formula:
Advantages of the present invention compared to the prior art is as follows:
1. 1.25% dye as compared to 25+% in Ms Clairol, Nice and Easy.
2. Ammonia smell is minimal as compared to competition, although our product does not contain any fragrance.
3. Dyes strong in the MEA system and faster vs. the ammonia system.
4. Dye penetration further into the hair shaft giving increased dye penetration and a longer wearing color.
5. Formulation is much simpler than competition, 10 ingredients compared to 20+ plus extracts and fluff.
6. Very appropriate for a potential Men's line with a shorter development line required.
7. Might be able to combined color base with peroxide in one bottle and ½ oz bottle or tube to begin the development.
8. Staining of the skin is very slight as compared to competition.
9. Damage to the hair a minimum, as dyeing is faster thereby having a shorter oxidation time during development.
10. Shorter risk of harm from dyes entering the skin and body as the skin and body as the percentages is reduced.
11. Warn wearing (red shift) is reduced as more dye is in the hair shaft. At the end of 30 days women will still need hair colored, as growth is ½ per month but red tones will not be invisible.
12. Shampoo and conditioner are specially formulated to give maximum cleaning with least amount dye wash out.
Conditioner is formulated to maintain luster, wet comb, detangle and import a smooth feel.
13. Formulation can be produced cheaper as quantities are increased.
14. Well suited for dyeing negro, Mexican hair (very thick) to black Shade.

SUMMARY OF THE INVENTION

A new and improvement hair dye formula is disclosed which is oleic acid free and contains a high percentage water base thus alleviating many prior art symptoms and unwanted side affects to the consumer.

Professionally Blended Benefits:
Why Water Based Hair Color
Professionally blended with true custom colors taking the guess work of selecting your shade.
All colors are Ammonia free.
No chemicals reaction that will cause damage to hair shaft.
No dryness to the hair follicles.
Professionally custom blended browns and blonds that are true to tone.
Color Me Quick colors are a selection of dark brown, medium brown, light brown and two selections of blondes medium and light.
Professionally custom blended for salt and pepper hair, gray hair so it reduces and eliminates brassiness.
Color Me Quick professionally custom blended Auburn's come in two selections dark and medium.
Color Me Quick professionally custom blends will not leave your hair with red roots and brown ends.
As time progresses the Color Me Quick color remains true and retains it shine.
All of the Color Me Quick professionally custom blended permanent color products treat your hair as gently as semi-permanent colors. While affording you complete coverage.
Color Me Quick's color lines are as gentle and less damaging to your hair because of the way they are custom blended and they are Ammonia free.
Professionally Blended Sulfate Free Benefits
Why Sulfate Free Shampoo and Conditioners
All of the Color Me Quick's shampoos and conditions are completely free of Sulfates ("Color Me Quick" is the inventor's trademark for this invention)
Sodium Lauryl Sulfate (SLS)
Sodium Laureth Sulfate (SLES)
Ninety percent of shampoos and beauty products contain these Sulfates.
SLS is not natural and products containing it should not be labeled as natural.
SlS is a while powder that is used as an inexpensive detergent because it produces plenty of foam and bubbles.
SlS is a strong degreaser that dries the scalp, skin and hair and is also an irritant.
SLS cleansers, corrodes hair and strips all of the protective lipids from the surface of the scalp, impending its ability to regulate moisture.
SLS is harmful if, left on hair to long, inhaled or swallowed. If accumulated in the eyes it said that it can cause eye damage.
SLS is systemic which means it is absorbed into the internal organs and is suspect that it can accumulate in the lungs, liver and brain.
Other uses for SLS as a concrete cleaner and engine degreaser.

Get the results you want with the Color Me Quick Professional Hair Care Products
Professionally Blended True Custom Colors Take the Guess Work Out of Selecting your Shade and are Ammonia Free
Shampoo and Conditioner Products are Completely Sulfate Free
In Home Professionally Formulated Hair Care Products at a Fraction of Salon Costs
No Unpleasant Odor from Ammonia
Color Lasts Four to Six Weeks—Just Like Salon Treatment The advantages and features discussed above and other advantages and features will become apparent from the detailed description of the best mode for carrying out the invention that follows.

DETAILED DESCRIPTION OF THE EMBODIMENT

Detailed reference will now be made to the preferred embodiments of the present invention, examples of which are illustrated in the accompanying formula tables.

Oleic Acid Free Formula:

| Part A (all percentages are by weight) | |
|---|---|
| 1-Water | 70-90% |
| 2-Carbomer | 0.5-3.50% |
| 5-Dipropylene Glycol | 1-5.00% |
| 6-Sodium Dioctyl Sulfosuccinate | 0.5-3.50% |
| 7-Sodium Lauryl Sulfate | 0.5-3.50% |
| 8-Sodium Lauryl Sulfoacetate and Disodium Laureth Sulfosuccinate | 0.5-3.50% |
| 9-Ethanolamine | 1-5.00% |
| 10-EDTA | 0.5-2.00% |
| 11-Color additives, Oxidation Dyes | 0.5-5.00% |
| Part B | |
| 1-Hydrogen Peroxide | 2-9.00% |
| 2-Carbomer | 0.5-3.50% |
| 3-EDTA | 0.5-2.00% |

Part A Mixing Procedure
1—In appropriate size kettle charge with water, add carbopol slowly with mixing until all is in solution.
2—Increase temperature to 120 degrees F.
3—Add remainder of part A slowly keeping all in solution and well mixed.
4—Add Ethanolamine, Maintaining pH not higher than 10.
Part B Mixing Procedure:
In separate kettle of suitable size, prepare part B.

| 1-Hydrogen Peroxide | 85-95% |
|---|---|
| 2-Carbomer | 0.5-3.5% |
| 3-EDTA | 0.5-2.00% |

Mixing Procedure
1—Charge kettle with appropriate amount of hydrogen peroxide.
2—Slowly Mix in carbomer with mixing and dissolve completely.
3—Add EDTA slowly and dissolve completely.

Procedure by Consumer:

Getting Ready To Color
Before stating:
Put on gloves
Place towel over shoulders to protect clothing and bare areas
Have timer ready
Comb hair to remove any entanglements
Do not wash hair prior to dyeing.
Hair must be dry when applying color.
First—Mix Color
It is recommended a strand test be performed prior to the actually dyeing, to determine the amount of time needed for your hair. All hair depending on its condition (thick, very gray, or highly process and damage) may require shorter or somewhat more time to obtain the desired results. A history of testing has shown a range of 8 to 12 minutes, in very rare occasions a maximum of 15 minutes has been used but this will make the hair darker than may be desired.
Procedure:
(Bottle A contains the above Part A formula along with the dye shades. Bottle B contains the above Part B formula with the activator ingredients.)
1. Empty entire contents of bottle A into the larger bottle B.
2. Secure cap on bottle B mixture and shake vigorously until color is evenly mixed, about 10-20 seconds.
3. Apply entire contents of bottle B onto head, working in with hands or comb, any due, which may stain skin, should be removed with soap and warm water. Part hair into sections as you apply color. Check hair is completely saturated and work though but do not rub into scalp.
4. After entire bottle has been applied set timer for ten minutes.
5. At end of time rinse hair with warm water and follow with shampoo to remove any additional product.
6. Dry and comb hair as normal.
7. Any unused hair color must be thrown away as it will lose its effectiveness.

Some hair due to damage, thickness and amount of gray may require less or more time, experience has shown the range to be within 8-12 minutes, 15 minutes being the maximum as the hair will continue absorbing color and may give a darker shade than desired.

The foregoing description of the embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

I claim:
1. A hair dye composition to be used as a mixture of a first part containing an alkali agent and a second part containing an oxidizing agent, wherein the composition comprises the following components (a) to (b):
   (a) water 70 to 90 wt. %; carbomer 0.5 to 3.50 wt. %, dipropylene glycol 1.0 to 5.00 wt. %, sodium dioctyl sulfosuccinate 0.5 to 3.50 wt. %, sodium lauryl sulfate and sodium lauryl sulfoacetate 0.5 to 3.50 wt. %, disodium laureth sulfosuccinate 0.5 to 3.50 wt. %, ethanolamine 1.0 to 5.00 wt. %, EDTA 0.5 to 2.00 wt. %, and color additives and oxidation dyes 0.5 to 5.00 wt. %, and
   (b) hydrogen peroxide 2.0 to 9.00 wt. %, carbomer 0.5 to 3.50 wt. %, and EDTA 0.5 to 2.00 wt. %;
wherein said mixture is for hair coloring.

* * * * *